United States Patent [19]

Schlein

[11] Patent Number: 4,780,361
[45] Date of Patent: Oct. 25, 1988

[54] LAMINATED SCRUB PAD HAVING AN ABRASIVE SURFACE

[76] Inventor: Allen P. Schlein, 107 Curtis Terr., Fairfield, Conn. 06432

[21] Appl. No.: 91,200

[22] Filed: Aug. 31, 1987

Related U.S. Application Data

[63] Continuation-in-part of Ser. No. 891,899, Aug. 1, 1986, abandoned.

[51] Int. Cl.$^4$ .............................................. B32B 27/34
[52] U.S. Cl. ..................................... 428/287; 156/79; 156/272.2; 156/285; 156/333; 428/311.7; 428/316.6; 428/317.1; 428/317.7; 428/317.9
[58] Field of Search ................. 428/287, 311.7, 316.6, 428/317.1, 317.7, 317.9, 906; 156/79, 272.2, 285, 334

[56] References Cited

U.S. PATENT DOCUMENTS 4,518,649 5/1985 Wang et al. ......................... 428/287

Primary Examiner—Marion C. McCamish
Attorney, Agent, or Firm—Spencer E. Olson

[57] ABSTRACT

A scrub pad, particularly suitable for medical uses, comprises a flattened laminate consisting of an initially compressed-in-thickness sheet of cellulose sponge material which upon absorption of washing fluids expands in thickness to approximately six times its original compressed thickness to which is bonded a sheet of mildly abrasive non-woven fabric formed of randomly oriented spray bonded synthetic fibers. In one embodiment the sponge and fabric layers are bonded together by a non-toxic heat- and pressure-sensitive acrylic resin. In another, presently preferred, embodiment the layers are joined by a cured formulation comprising selected proportions of a water activated polyurethane gel, an aqueous solution of a liquid detergent and crystalline iodine which, when wetted, releases the antiseptic detergent while retaining the bond between the sponge and fabric.

13 Claims, 1 Drawing Sheet

LAMINATED SCRUB PAD HAVING AN ABRASIVE SURFACE

This application is a continuation-in-part of application Ser. No. 891,899 filed Aug. 1, 1986, now abandoned.

BACKGROUND OF THE INVENTION

This invention relates generally to scrub pads suitable for medical use and, more particularly, to a scrub pad consisting of a flat laminate of initially compressed-in-thickness cellulose sponge material and a thin layer of an abrasive fabric bonded thereto, and methods for producing the same.

Scrub pads consisting in whole or in part of cellulose sponge material are available in a variety of forms, the characteristics of which largely depend on their intended use, ranging from pads consisting of only cellulose sponge material in sheet form, either expanded or compressed, to expanded sponge materials having an abrasive backing, such as the "Rescue" and "Scotch Brite" scrub pads marketed by Minnesota Mining and Manufacturing Company.

Another type of available cleaning pad consists of a ball of entangled synthetic resin fibers, specific examples of which are the product marketed under the trademark "Tuffy" by the Household Products Division of Miles Laboratories, Inc. of Chicago, Ill., and the pad manufactured by Glencourt Inc. of Walnut Creek, Calif. and sold under the tradename "Jumbo Scourer" and labeled a "knitted plastic mesh". Such pads are used primarily for the scrubbing of dishes, pots and pans and generally are too abrasive to be used in medical applications even if the synethetic resin fibers were otherwise medically acceptable.

Cellulose sponges are commercially available and widely used for medical purposes, such as in operating rooms, because they can be sterilized and are capable of absorbing a large amount of liquid (e.g., an antiseptic washing solution). However, because of the soft texture of the sponge when wet, it is not sufficiently abrasive to effectively remove inground dirt, grime or blood from a wound or from the hands of the doctor. Available sponge products with abrasive backings, such as the above-mentioned "Rescue" and "Scotch Brite" pads, are not acceptable for medical purposes, creating a need for a medically acceptable scrub pad capable of releasably absorbing substantial quantities of washing liquid and also having an abrasive surface. Additionally, the pad should be as thin as possible for minimizing the space required for storing a reasonable supply of sponges and, indirectly to reduce the cost of shipping and storage. This requirement is of particular significance to the operation of the far-flung medical facilities of the Armed Services of the United States which often requires shipment, on short notice, of sponge products to containerized hospitals around the world; the physical size of the expanded cellulose sponges heretofore available has caused concern not only in the respect of shipping costs, but the space required for their storage and the cost of providing such space in a facility already cramped for space.

Accordingly, it is a primary object of the present invention to provide an improved sponge scrub pad suitable for medical use which has an abrasive surface and a smaller volume than previously available sponges.

Another object of the invention is to provide relatively simple and inexpensive processes for manufacturing the improved scrub pad.

SUMMARY OF THE INVENTION

Briefly, the scrub pad according to the invention is an elongated flattened body having two major surfaces of approximately the same size, the first of the surfaces being composed of randomly oriented mildly abrasive synthetic fibers spray bonded to form a non-woven fabric layer and the second major surface being composed of a layer of initially compressed-in-thickness cellulose sponge material which expands in thickness upon initial contact to washing fluids to approximately six times its original, compressed thickness. The sponge and fabric layers are adhesively secured together over their entire surfaces with a suitable medically acceptable adhesive. The layer of sponge material preferably is a commercially available medically acceptable cellular sponge material in compressed form, and the fabric layer preferably is a commercially available non-woven fabric composed of randomly oriented spray bonded polyester fibers of the kind extensively used in medical applications such as for surgical gowns and drapes for operating tables.

One process for manufacturing the improved scrub pad includes the steps of sandwiching a sheet of heat- and pressure-sensitive material, such as acrylic resin, between a sheet of initially compressed-in-thickness cellulose sponge material and a sheet of non-woven polyester fiber fabric. The sandwiched sheets are subjected to a combination of temperature and pressure, as by passing it between high pressure heated rollers, selected to cause the acrylic resin to soften and thereby bond the layer of sponge material to the fabric layer and, at the same time, to further compress-in-thickness both the sponge material and the fabric to produce a laminate of minimal thickness. The laminate is then cut into suitably sized pads, individually packaged in sealed envelopes and sterilized by ionizing radiation or ethyl oxide gas.

According to another process for manufacturing the scrub pad, the sheet of initially compressed-in-thickness cellulose sponge material is bonded to a sheet of non-woven abrasive synthetic fiber material with a formulation consisting of selected proportions of a water activated polyurethane gel and an aqueous solution of a medication, cosmetic or detergent. This formulation, which is highly viscous when initially mixed, is applied in a thin coating on one surface of the initially compressed sponge material and the fabric sheet is then placed upon and pressed into firm contact with the coating. The formulation quickly cures to form a hard thin layer which is strongly bonded to the initially compressed cellulose sponge and to the fiber fabric sheet, the resulting laminate being then cut into pads of suitable size and packaged.

Other objects, features and advantages of the invention, and a better understanding of its structure and methods for making it, will be had from the following detailed description, taken in conjunction with the accompanying drawings.

DESCRIPTION OF THE PREFERRED EMBODIMENT

Figure 1:
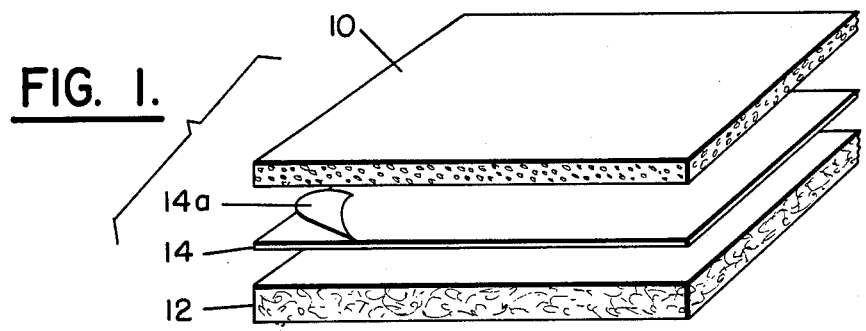
FIG. 1 is a fragmentary perspective view showing the components of a first embodiment of the scrub pad prior to lamination.

Referring to FIG. 1, the scrub pad according to one embodiment of the invention is formed by bonding a sheet 10 of initially compressed-in-thickness cellulose material, which is commercially available from O'Cello Corporation in sheets approximately ⅛" thick, to a sheet 12 of non-woven synthetic fiber fabric with a suitable adhesive, such as a sheet 14 of pressure- and heat-sensitive acrylic resin material. The sponge material is made with a plasticizer of Sorbitol, essentially a sugar product, which makes the material acceptable for medical use, and is preferably white in color. As received from the vendor the sponge material is compressed to a thickness of about ⅛" from its normal expanded thickness of about ¾ inch; that is to say, the initial compressed thickness is approximately one-sixth the thickness to which it expands when wetted by a washing liquid. The layer 12 is preferably a known non-woven, spray-bonded polyester fabric of the type used in such medical applications as surgical gowns, sheets and drapes for operating tables. The material is commercially available from Loran Products division of Turco Purex Industrial Corp. of Lawrence, Mass., as its product No. M-93 Light Duty white, and as received from the vendor is slightly less than ¼" thick. Alternatively, non-woven fabrics made with other synthetic fibers such as nylon and dacron may be used.

Applicant has discovered that in spite of the differences in surface characteristics between the compressed cellulose sponge and the non-woven spray-bonded polyester fabric, they can be securely bonded one to the other with a heat- and pressure-sensitive acrylic resin of the type commercially available in sheet form from Adcom Corporation, Westbury, N.Y., as its Product Number 5131, having a peelable protection backing 14a affixed to one surface thereof, which is removed before the sheet 14 is placed between the compressed sponge and synthetic fiber sheets.

Figure 2:
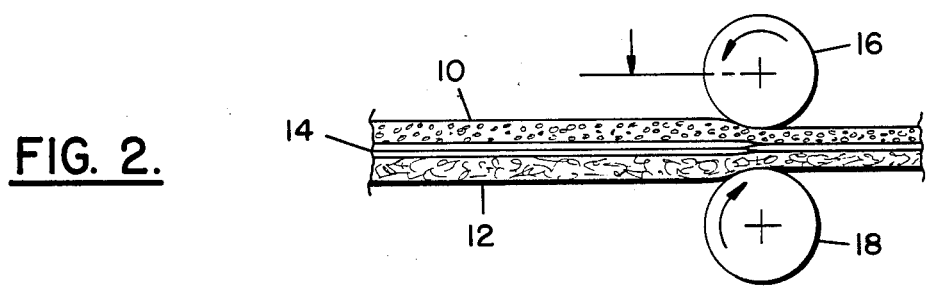
FIG. 2 is a schematic illustration of apparatus for laminating the components shown in FIG. 1.

As schematically shown in FIG. 2, the sandwiched initially compressed-in-thickness cellulose sponge layer 10, the sheet 14 of acrylic resin material and layer 12 of spray bonded polyester fabric are presented to and rolled between a pair of spaced apart heated rollers 16 and 18 which not only further compress the already compressed sponge to some degree and also compress the polyester fabric material somewhat but also cause softening and curing of the acrylic resin material to provide a firm mechanical bond between the compressed sponge and the synthetic fiber fabric. Pressures of the order of 2000 pounds per square inch, a temperature in the range of about 325° F. to 400° F., and a transport speed of the order of 8 to 12 feet per minute has proved to be a suitable combination of parameters for effecting lamination of the sandwiched components. It is to be understood, however, that these values are by way of example only and that depending on the nature of the laminating equipment and the desired thickness of the laminate other operating parameters will be suitable. Preferably, the thickness of the finished laminate is of the order of ⅛" to 3/16", a significant reduction from the approximately ⅜" combined thickness of the starting components, namely, the compressed-in-thickness cellulose sponge layer and the layer of spray-bonded synthetic fiber fabric.

Figure 3:
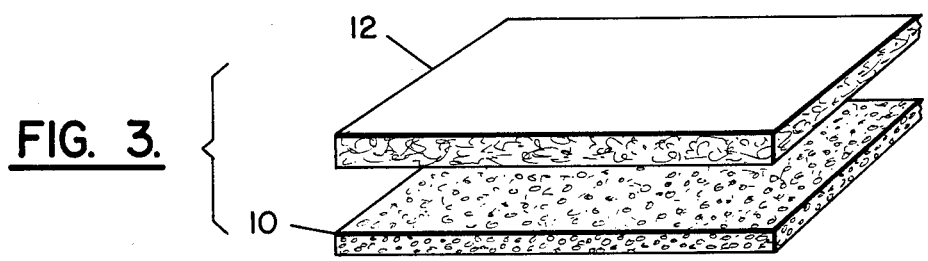
FIG. 3 is a fragmentary perspective view illustrating the components of a second embodiment of the scrub pad.

Referring now to FIG. 3, the scrub pad according to another embodiment of the invention, which contains an antiseptic soap, is formed by bonding a sheet of compressed cellulose sponge material 10, typically initially compressed to approximately one-sixth its thickness when expanded upon contact with washing fluids, is bonded to a sheet 12 of mildly abrasive non-woven, spray bonded synthetic fiber fabric with a formulation consisting of a water activated polyurethane gel, an aqueous solution of a high foaming liquid detergent and iodine crystals in such relative proportions that the formulation is highly viscous when the ingredients are initially mixed together at room temperature and quickly cures when thinly spread. The polyurethane gel may be HYPOL, a product available from W. R. Grace, which has long been used as a vehicle for imbedding soap in cellulose sponges; the liquid detergent may be Hamposyl, another W. R. Grace product useful in medical applications; and the iodine may be Povidon iodine, a crystalline form of iodine, such as the BASF product PVP-Iod 30/06, in the following relative proportions:

HYPOL—35 gr.
Povidon iodine—45 gr.
Hamposyl—75 gr.

These relative proportions satisfy Food and Drug Administration requirements that when the sponge is wetted the resulting iodine solution should be approximately a 10% solution by weight and releasing 1% free iodine ions in solution. The formulation is prepared by first mixing the dry iodine crystals with the very viscous polyurethane gel and then mixing in the Hampsyl, which causes the mixture to foam. The resulting formulation is foamy, reddish brown in color, and has a room temperature viscosity which permits it to be applied as a thin coating. For best results, one surface of a sheet of initially compressed-in-thickness cellulose sponge material is thinly coated with the formulation, the theory being that a slight amount of free water in the coating slightly opens the pores of the compressed cellulose so as to to allow some penetration of the formulation, and then attaching the sheet of spray bonded synthetic fiber fabric to the coating; because the texture of the fabric is already quite open, the formulation easily penetrates the confronting surface of the fabric. The initial tackiness of the formulation holds the two layers together, and the final bond may be improved by applying pressure to the laminate. The thin coating of the formulation, a thickness of less than ⅛" being sufficient, cures in about a minute to form a hard, albeit relatively flexible, layer which forms a strong mechanical bond between the two layers of disparate materials.

Figure 4:
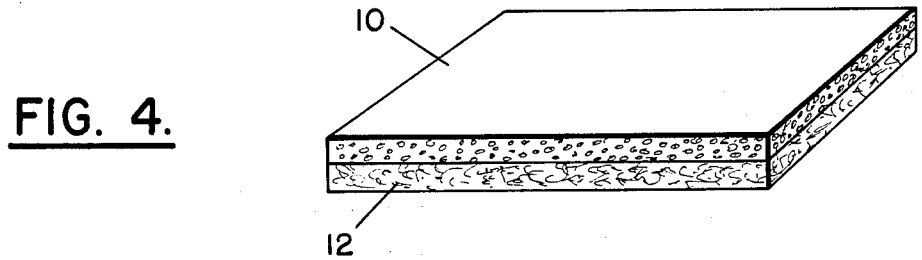
FIG. 4 is a perspective view of a completed scrub pad, ready for packaging.

The completed laminate, by whichever method, usually will have an area determined by the available size of sheets of compressed cellulose sponge material, typically 9"×36", is then cut up into pads of suitable size, 2"×3" being typical. The completed pad, shown essentially full size in FIG. 4, is then sealed in a suitable package and then sterilized by ionizing radiation or ethylene oxide gas. It is seen that the individual scrub pads have a very small volume, thus permitting a large number of them to be stored in a very small space, whether for shipment or in a medical facility, and making them particularly attractive for use in "prep kits" for operating room use. By way of comparison, typical available sponge-brushes for preoperative scrubbing are 3½" long by 1⅞" wide by 1⅞" thick, and thus have a volume of 12.3 cubic inches, about eight times greater than the maximum volume of 1.5 cubic inches for a 2" by 3" scrub pad according to the present invention.

Figure 5:
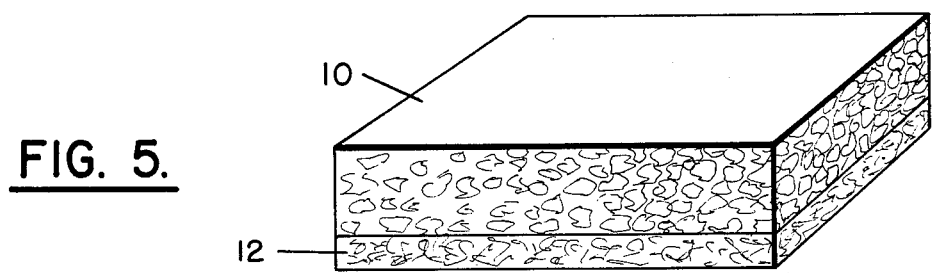
FIG. 5 is a perspective view illustrating the relative thicknesses of the expanded cellulose sponge material and the non-woven fabric after absorption of a liquid.

Although the cellulose sponge material is greatly compressed, this does not affect its capability to absorb a large quantity of liquid and expand in thickness. As depicted in FIG. 5, when the sponge material 10 contacts a washing liquid it expands to a thickness of about ¾" from its initial compressed thickness of approximately ⅛" in the dry laminate shown in FIG. 4. When wetted by a washing liquid, the sponge surface of the pad is very soft, but the surface covered by synthetic fiber fabric layer 12, which does not expand to any significant extent when wet, is sufficiently abrasive to effectively remove dirt or grease or the like. When the scrub pad bonded together by the detergent-containing formulation is wetted by water the detergent, rendered antiseptic by the iodine, is released without, however, affecting the bond between the expanded sponge material and the fabric layer 12.

It is also within the contemplation of the invention to add a detergent, cosmetic, medication or an antiseptic soap to the resin-bonded embodiment of the scrub pad. This may be accomplished by either dipping the polyester fiber fabric 12 in or spraying it with a suitable aqueous solution of the detergent, cosmetic, medication or soap and allowing it to dry before laminating it with the compressed sponge material.

Although the scrub pad and the methods for making same have been described in the context of its medical application, it is to be understood that the principles of the invention can be used to make scrub pads for non-medical applications as well. For example, it is within the contemplation of the invention to laminate the described non-woven polyester fabric, using the same acrylic resin sheet material, such as that marketed in sheet form by Spontex Corporation of Columbia, Tenn. This sponge material is made using diethylene glycol as the plasticizer which, although medically unacceptable because of its toxicity, is perfectly safe and has been approved for the cleaning of kitchens and even food-handling machines. The sponge material being safe for general cleaning purposes, the scrub pad according to the invention is likewise safe because the aforesaid spray bonded polyester fiber fabric has been approved for medical purposes and is therefore clearly acceptable for general cleaning applications.

Although preferred methods of laminating the components of the scrub pad have been described, it will be evident to ones skilled in the art that the components of the scrub pad can be laminated by other methods and/or machinery than those suggested. It is also within the contemplation of the invention that in the manufacture of scrub pads for non-medical applications, adhesives other than the described acrylic resin sheet material, such as heat-curable glues, may be used to secure the polyester fabric to the compressed sponge material.

I claim:

1. A scrub pad comprising a flattened laminate having two major surfaces of the same size, the first of said surfaces being composed of randomly oriented mildly abrasive spray bonded synthetic fibers forming a non-woven fabric layer and the second major surface being composed of a layer of initially compressed-in-thickness cellulose sponge material which expands in thickness upon initial contact with washing fluids to approximately six times its original compressed thickness; and
   means adhesively securing substantially the entire area of said first and second major surfaces together.

2. A scrub pad as defined by claim 1, wherein said means for adhesively securing is heat- and pressure-sensitive acrylic resin material disposed between said fabric and sponge material layers and cured by subjecting said laminate to selected temperature and pressure.

3. A scrub pad as defined by claim 2 suitable for medical use, wherein said layer of sponge material is medically acceptable cellulose sponge material having an initial compressed thickness of about one-eighth inch,
   wherein said fabric layer is composed of a medically acceptable non-woven fabric, and
   wherein said acrylic resin is a non-toxic, medically acceptable acrylic resin.

4. A scrub pad as defined by claim 1, wherein said means for adhesively securing is a cured formulation comprising in selected proportions at least a water activated polyurethane gel and an aqueous solution of a constituent selected from the group consisting of detergents, cosmetics and medications, which formulation dissolves upon contact with washing fluids and is absorbed by the expanded sponge material.

5. A scrub pad as defined by claim 4, wherein said layer of sponge material is medically acceptable cellulose sponge material,
   wherein said fabric layer is composed of a medically acceptable non-woven fabric, and
   wherein said formulation comprises water activated polyurethane gel, an aqueous solution of a detergent and crystalline iodine in such proportions that when mixed the formulation initially has a room temperature viscosity which permits it to be thinly coated and to then rapidly cure to form a strong bond between said sponge material and said non-woven fabric.

6. A scrub pad as defined by claim 5, wherein said formulation comprises the following ingredients in about the indicated relative proportions:
   water activated polyurethane gel—35 grams
   liquid detergent (aqueous solution)—75 grams
   Povidon iodine—45 grams.

7. A scrub pad as defined by claim 6, wherein said layer of sponge material has an initial compressed thickness of about one-eighth inch.

8. A method of manufacturing a scrub pad having two major surfaces of different materials comprising the steps of:
   forming a first major surface from a non-woven abrasive fabric of randomly oriented spray bonded synthetic fibers,
   forming a second major surface from a sheet of initially compressed-in-thickness cellulose sponge material which expands in thickness upon contact with washing fluids to approximately six times its original compressed thickness,
   assembled said two major surfaces together with a layer of adhesive material sandwiched therebetween,
   pressing said sandwiched layers together so as to cure said adhesive material and secure said fabric layer to said layer of sponge material whereby to form a laminate which is much thinner than the thickness to which it expands upon absorption of washing fluids, and cutting said laminate into suitably sized pads.

9. A method of manufacturing a scrub pad as defined by claim 8, wherein said layer of adhesive material is a sheet of temperature- and pressure-sensitive acrylic resin, and wherein said sandwiched layers are pressed together by passing the sandwiched layers between heated pressure rollers.

10. A method of manufacturing a scrub pad as defined by claim 8, wherein said method includes, prior to the step of assembling said two major surfaces together, the step of coating one surface of said sheet of compressed sponge material with an adhesive material composed of a formulation comprising selected proportions of at least a water activated polyurethane gel and an aqueous solution of a constituent selected from the group consisting of cosmetics, medications and detergents which cures to form a bond to secure said major surfaces together.

11. A method of manufacturing a scrub pad having two major surfaces of different materials comprising the steps of:

forming a first major surface from a relatively thin sheet of mildly abrasive fabric formed of randomly oriented spray bonded synthetic fibers, forming a second major surface from a sheet of cellulose sponge material initially compressed-in-thickness to about the thickness of said fabric sheet which upon contact with washing fluids expands to approximately six times its original compressed thickness, coating one surface of said sheet of compressed sponge material with a formulation comprising selected proportions of at least a water activated polyurethane gel and an aqueous solution of a detergent, assembling said sheets of fabric and sponge material with said formulation coating sandwiched therebetween, pressing said sandwiched sheets together for a period of time sufficient to cure said formulation so as to secure said major surfaces together over their common area whereby to form a laminate which is much thinner than the thickness to which it expands upon absorption of washing fluids by said sponge material, and cutting said laminate into pads of suitable size.

12. A method of manufacturing a scrub pad as defined by claim 11, wherein said formulation further comprises a selected proportion of iodine crystals.

13. A method of manufacturing a scrub pad as defined in claim 11, wherein said sheet of sponge material is formed to have an initial compressed thickness of about one-eighth inch, wherein said sheet of non-woven fabric is formed to have an initial thickness of less than about one-fourth inch, and wherein said formulation for coating at least one of said sheets comprises the following ingredients in about the indicated relative proportions:

water activated polyurethane gel—35 grams
liquid detergent (aqueous solution)—75 grams
Povidon iodine—45 gram.

* * * * *